United States Patent [19]
Lieberman

[11] Patent Number: 5,800,532
[45] Date of Patent: Sep. 1, 1998

[54] ASYMMETRIC INTRAOCULAR LENS

[75] Inventor: David M. Lieberman, New York, N.Y.

[73] Assignee: Scientific Optics, Inc., New York, N.Y.

[21] Appl. No.: 804,254

[22] Filed: Feb. 21, 1997

Related U.S. Application Data

[63] Continuation of Ser. No. 469,488, Jun. 6, 1995, abandoned.

[51] Int. Cl.$^6$ .................................................. A61F 2/16
[52] U.S. Cl. ................................................. 623/6; 351/161
[58] Field of Search ............................ 623/6; 351/160 R, 351/161

[56] References Cited

U.S. PATENT DOCUMENTS

| | | | |
|---|---|---|---|
| 4,010,496 | 3/1977 | Neefe | 623/6 |
| 4,512,039 | 4/1985 | Lieberman | 623/6 |
| 4,525,043 | 6/1985 | Bronstein . | |
| 4,580,882 | 4/1986 | Nuchman et al. . | |
| 4,581,031 | 4/1986 | Koziol et al. | 623/6 |
| 4,648,878 | 3/1987 | Kelman | 623/6 |
| 4,702,573 | 10/1987 | Morstad | 351/161 |
| 4,769,033 | 9/1988 | Nordan | 623/6 |
| 4,798,609 | 1/1989 | Grendahl . | |
| 4,906,245 | 3/1990 | Grendahl | 623/6 |
| 5,019,098 | 5/1991 | Mercier . | |
| 5,020,898 | 6/1991 | Townsley | 351/160 R |
| 5,125,729 | 6/1992 | Mercure | 351/161 |
| 5,141,301 | 8/1992 | Morstad | 351/161 |
| 5,173,723 | 12/1992 | Volk . | |
| 5,198,844 | 3/1993 | Roffman et al. . | |
| 5,214,453 | 5/1993 | Giovanzana . | |
| 5,245,366 | 9/1993 | Svochak | 351/161 |

FOREIGN PATENT DOCUMENTS 0008726  3/1980  European Pat. Off. ................ 351/161

OTHER PUBLICATIONS

Polytech Contact Lens Systems, *Clinica*, 425:15, Oct. 31, 1990, "Tailor–Made Contact Lenses Reach U.K.".

*Opthalmology Times*, p. 8, Jul. 15, 1990, "Corneal Modeling Aids Contact Lens Fitting For Keratoconus.".

Bethke, W., *Review of Opthalmology*, 9:34–35, Dec. 1994, "What's New in Contact Lenses.".

*Primary Examiner*—Mary Beth Jones
*Attorney, Agent, or Firm*—Darby & Darby

[57] ABSTRACT

An intraocular lens is disclosed which includes a central portion having a first refractive power region and a peripheral portion having a second refractive power region. The second refractive power region is substantially concentrated only in one predetermined location; or is asymmetrically disposed on the inferior nasal quadrant of the intraocular lens. In a preferred configuration, the second refractive power region has more refractive power than the first refractive power region. Preferred configurations may additionally or alternatively include a toric surface and/or a prism.

21 Claims, 3 Drawing Sheets

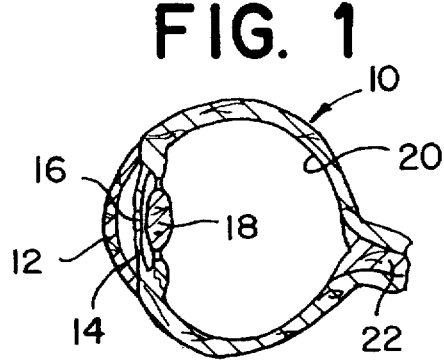
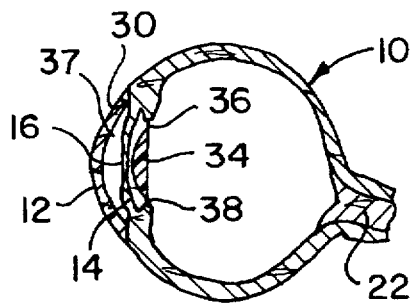
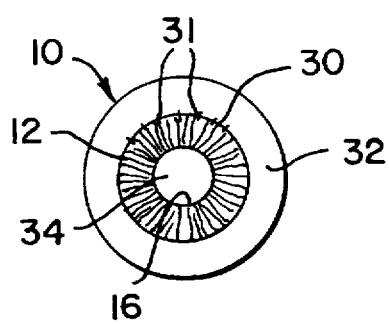
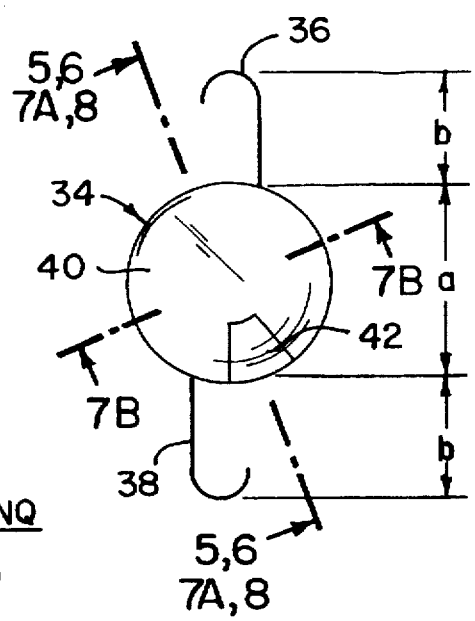
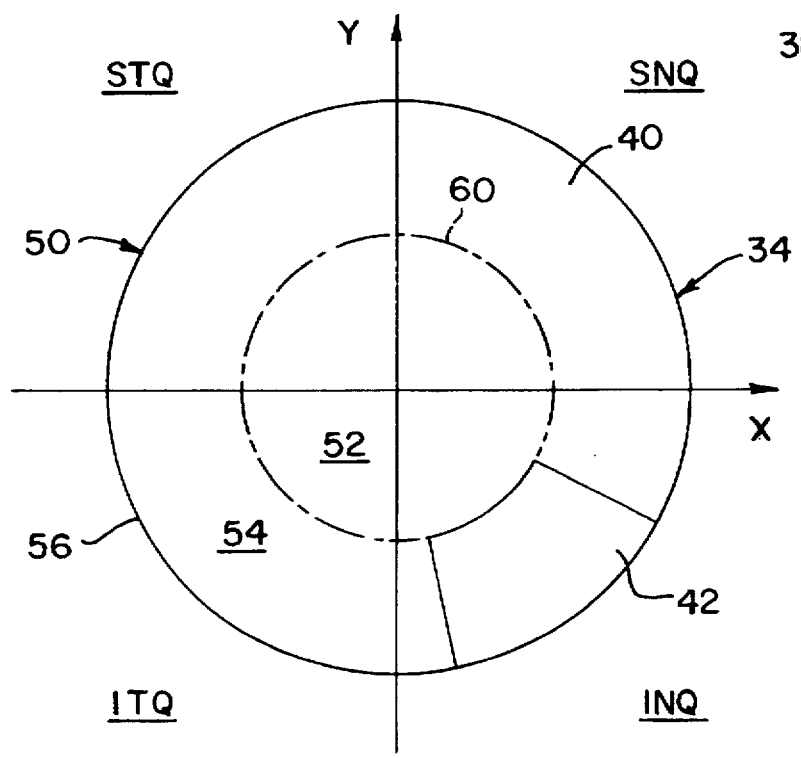

ASYMMETRIC INTRAOCULAR LENS

This is a continuation of application Ser. No. 08/469,488, filed Jun. 6, 1995, now abandoned.

FIELD OF THE INVENTION

The present invention relates to an intraocular lens, and more particularly, to a bifocal intraocular lens in which a segment of relatively greater optical power is disposed along a peripheral portion in an asymmetric manner, and, primarily the nasal quadrant of the intraocular lens.

BACKGROUND OF THE INVENTION

The normal crystalline lens of the human eye anatomically lies behind the iris and in front of the vitreous face, a space commonly referred to as the "posterior chamber." The "anterior chamber" is that space between the iris and the posterior surface of the cornea. The opening within the iris defines the pupil. Various conditions cause the pupil to dilate and constrict. For example, the pupil dilates in low light and constricts in relatively brighter light. In addition, the pupil dilates when a person looks at a distant object whereas it constricts when the person views a near object. The healthy, crystalline lens is clear and does not distort or interfere with the light impinging on the retina. The normal lens has opposed convex generally spherical surfaces.

The crystalline lens contributes approximately twenty percent of the necessary refractive power within the eye to properly focus an image on the retina; the cornea is responsible for about the remaining eighty percent. Other optical elements of the eye include a fluid within the anterior and posterior chambers and the vitreous body. These optical elements contribute only a minor component of the refractive power and are not discussed in order to simplify the present description. The various refractive elements of the eye cooperate to focus light on the sensory retina which, in turn, converts the light energy to electrical energy. The electrical energy is transmitted to the central nervous system which autonomically filters the various signals (from whatever source or location) to enable the "best image" to be perceived. Additionally, the central nervous system autonomically selects the optimal portion of the cornea and crystalline lens to best focus the object of interest. The exact mechanism by which the central nervous system interprets the signals generated by the eye is complex and poorly understood and, in any event, is not pertinent to the present description.

When the eye "sees" an object, it is viewing light that is reflected from the object. The light enters the eye at the corneal plane and is refracted by the cornea/lens system onto the retina. The eye needs about sixty diopters to focus an object at infinity onto the retina. Of course, some eyes need less power to focus the distant object onto the retina (as in myopia) and some eyes need more power to focus the distant object (as in hyperemia). In addition, the eye requires three or so additional diopters to view near objects. However, the cornea is fixed and not capable of any change in its refractive power. Rather, it is the crystalline lens that contributes the additional refractive power for near-field activities such as reading. The lens of the aging eye gradually loses its flexibility until it can no longer "accommodate" or add the necessary power to view near objects. This process is commonly referred to as presbyopia, and generally predominates at about age forty and continues until the human lens is almost inelastic, at about age fifty-five. In addition, the previously clear elastic crystalline lens often becomes progressively opaque, a condition known as cataract.

Cataract surgery is performed when the lens has sufficiently clouded to interfere with the person's ability to engage in near-field or far-field activities, as dictated by the patent's career, hobbies, or life style. The cataractous lens is typically removed through a horizontal incision made at the superior part of the juncture of the clear cornea and the opaque sclera. Once the cataractous lens has been surgically removed, light is transmitted readily through the cornea onto the retina. However, as noted above, the crystalline lens of the eye performs a significant light focusing function. Consequently, once the lens is removed, the eye's optical system is left about twenty diopters "short," and the light is no longer properly focused onto the retina. Another lens or refracting element must be placed within the refracting system for the image to be properly focused.

Other clinical conditions that may co-exist or be induced by cataract surgery (for example, astigmatism in the cornea), that require correction for light to focus properly onto the retina. Astigmatism is the condition in which the eye does not enjoy spherical optics, that is, one optical axis of the eye is optically stronger than another. The net result is that light is defocused with respect to the retina. One method of correcting astigmatism is to place a toric intraocular lens within the lens to compensate for any preexisting and surgically induced spherical error. A toric lens is one in which has optical axes of differing powers. The toric lens is formed and oriented, as understood by those skilled in the art, to offset the astigmatism.

There have been continuing efforts to improve the rehabilitation of a patient's vision and lens system after removal of the crystalline lens. Intraocular lenses provide one type of optical aid being employed to refocus light onto the retina; others include spectacles and contact lenses. Conventional intraocular lenses ("IOLs") are either of a plano-convex or biconvex construction, with each curved surface defining a spherical section. The IOL is implanted in the eye through the same incision that is made to remove the cataractous lens. Customarily, IOLs are made of either polymethymethacryalate (PMMA) or silicone.

The healthy, natural lens of a twenty year old person is sufficiently elastic to alternate between reading (near-field) and distant (far-field) viewing without effort, owing to the lens' ability to change shape and thereby increase its net power by three or more diopters to view near-field objects. In contrast, IOLs lack any ability to change their shape to provide the necessary increase in dioptric power for near-field activities. Thus, recipients of single-focal length intraocular lenses have clear vision in either the near or distant field, but not both, unless spectacles are also used.

In an effort to address this problem, bifocal IOLs have been developed.

A customary bifocal lens is a lens that has two distinct focal lengths. For an object to be in focus at the plane of the retina, it must be at a distance corresponding to the focal length of the lens. Hence, a bifocal lens can focus objects that are at two distinct distances from the bifocal lens. Shorter focal length lenses have greater dioptric power than longer focal length lenses. The "power" of convergent lens' is inversely proportional to its focal length, so a lens having a meter focal length has a power of +1 diopter, whereas a lens having a 0.2 meter focal length has a power of +5 diopters. The power of a divergent lens is similarly inversely related to its focal length, but its power is expressed in negative (−) diopters.

An image is perceived as being "sharp" when all the optical elements of the optical system combine to produce a focused image on the retina. Various factors and elements contribute to the degree of relative sharpness. Such elements include but are not limited to dilation of the pupil, the distance of the object of regard (the object being viewed) with respect to the optical system, the net refractive power of the optical system, and the relative clarity of the various optical lens elements. For either focal length of a bifocal lens, there is a range of distances (depth of field) for which the object of regard will be perceived as reasonably sharply focused.

Conventional bifocal IOLs are constructed such that the very center of the lens has one power whereas a second power is disposed symmetrically about the periphery of the IOL. The latter provides near-field power to permit a near-field object to be focused onto the retina. Two types of bifocal IOLs have been developed. One is a diffractive multifocal implant which is available from Alcon Laboratories, Fort Worth, Tex. This IOL includes a radially and symmetrically displaced a diffractive element ("SDE") about the center of the IOL. This symmetric surface is placed about and on the posterior surface of the IOL and provides a surface that gives two focal lengths, one for viewing near-field objects and one for viewing far-field objects. The symmetric diffractive IOL is associated with diminished contrast sensitivity and blur, and this IOL has not yet been approved by the Federal Food and Drug Administration (FDA) for routine implantation in humans. Another known bifocal IOL is currently under investigation by Iovision, Inc. of Irvine, Calif. Iovision's design has a spherical central portion surrounded in a symmetrical manner by an aspheric peripheral portion of increased power. The peripheral portion can instead be spherical. All known bifocal IOLs have their additional refractive power symmetrically displaced about the complete periphery of the IOL.

Known bifocal IOL designs commonly cause distortion for patients when viewing distant objects in relatively low light conditions as in movie theaters or while driving a car at night. Some light rays pass through the very center of the IOL while others are affected by the more peripheral portions of the IOL. If the pupil is miotic or "small," only the central light rays pass through the IOL and the more peripheral rays are blocked by the iris. The very central light rays should be in focus at the retina. When the eye views a distant object, the pupil dilates and all rays from all aspects of the visual field enter the pupil, pass through the peripheral portion of the IOL, and ultimately impinge on the retina. As the peripheral portion of the bifocal IOL has a relatively higher dioptric power, the more peripheral light rays passing through the peripheral, additional-power portion of the bifocal IOL are defocused at the retina. The retina forwards the defocused and confusing information as electrical signals for interpretation as previously discussed. The net result of conventional bifocal IOLs is that there exists peripheral image blur for distant objects, or other image distortion such as glare, loss of contrast sensitivity, and halo effects, or a combination of these undesirable characteristics.

Near-field activities such as reading, cooking or personal hygiene are viewed only via light rays reflected from a nearby object being viewed, and those rays enter the eye primarily through the nasal portion of the eye. Unlike far-field activities, the light entering from the temporal, superior and most of the inferior aspects of the visual field is of no interest and thus autonomically ignored by the central nervous system.

Further, healthy, youthful eyes readily converge towards the nasal visual field for objects of regard in the near-field, whereas the convergence reflex of the eyes of an elderly patient is comparatively diminished. Convergence is required for near-field activities such as reading. The amount of convergence needed to view a near-field object is reduced by spectacles having a base-out prism because the base out prism of the spectacles provides a convergence assist relative to the nose. Conceptually, a "base-out" prism can be modeled as two adjacent prisms with their apexes touching (to appear like a bow tie pattern, as in a myope's spectacles). Because light is always reflected towards the base of a prism, the base-out prism displaces the image of the object being viewed on the cornea and thereby provides a desirable assist to the convergence reflex when viewing near-field objects. Intraocular lenses of conventional design are high-"plus" lenses and thus contribute an undesirable base-in prism effect, which opposes the desired convergence relative to the nose, as light enters and exits the lens. A "base-in" prism can generally be modelled as two adjacent prisms having their bases touching (to appear like a diamond pattern), and has the effect of reflecting light from an object being viewed away from the person's nose.

What is needed in the art and has heretofore not been provided is a bifocal IOL that avoids one or more of these problems, yet provides focused vision for both near-field and far-field objects of regard.

It is therefore one object of the present invention to provide an intraocular lens with a clearer and/or more accurate vision correction for both near-field and far-field objects.

It is a further object of the invention to provide an asymmetric, bifocal intraocular lens that can be economically manufactured.

SUMMARY OF THE INVENTION

One aspect of the invention is directed to a bifocal intraocular lens for implantation into an eye having an optical surface including a body portion and a peripheral portion, a first refractive power region within at least said body portion, and a second refractive power region located substantially within said peripheral portion and adapted to occupy at least a segment of a nasal quadrant of the intraocular lens relative to the eye, and adapted to be clear of a temporal quadrant of the intraocular lens relative to the eye, said second refractive power region being of greater refractive power than said first refractive power region.

More specific embodiments include without limitation one or more of the following variations:

(a) said first refractive power region is constructed for focusing far-field images on the retina, and said second refractive power region is constructed for focusing near-field images on the retina of the eye;

(b) said first refractive power region occupies a region of said peripheral portion outside said second refractive power region;

(c) said second refractive power region extends inwardly from a peripheral edge of the intraocular lens;

(d) said second refractive power region is adapted to occupy at least a segment of the inferior nasal aspect of the intraocular lens as placed relative to the eyes' location respective to the nose.

With reference to opposing anterior and posterior surfaces of the intraocular lens, even more specific embodiments include without limitation one or more of the following variations:

(a) said second refractive power region is disposed on either the anterior or posterior surface of the intraocular lens;

(b) the intraocular lens has a toric surface on either the anterior or posterior surface of the intraocular lens;

(c) said toric surface is on a surface of the intraocular lens that does not include at least one of said first and second refractive power regions;

(d) the intraocular lens has a purposefully placed prism on either of the anterior or posterior surfaces; and (e) said prism is disposed on a surface other than and opposite said second refractive power region.

According to a preferred embodiment, the invention provides a bifocal intraocular lens both for focusing images on a retina of an eye and for correcting astigmatism, the intraocular lens including a peripheral portion and a nasal quadrant and having anterior and posterior surfaces, first and second refractive power regions on one of said anterior and posterior surfaces, said first refractive power region being constructed for focusing far-field images on the retina, and said second refractive power region being constructed for focusing near-field images on the retina, said second refractive power region being asymmetrically disposed on the peripheral portion of the inferior nasal quadrant of the intraocular lens, and another of said anterior and posterior surfaces being torically shaped and having first and second meridians, one of said first and second meridians being optically weaker than the other.

More specific features of this embodiment include without limitation one or more of the following variations:

(a) the intraocular lens has a body portion outside said second refractive power region;

(b) the first refractive power region spans the inferior nasal quadrant of the intraocular lens;

(c) the intraocular lens has a prism disposed on the other side of said anterior and posterior surfaces and opposite said second refractive power region; and (d) said prism is disposed on the posterior surface of the intraocular lens and said second refractive power region is disposed on the anterior surface.

DESCRIPTION OF THE DRAWINGS

FIG. 1 is a cross-sectional right side view of a human eye prior to surgical removal of the lens;

FIG. 2 is a cross-sectional right side view of an eye after removal of the lens and implantation of an IOL;

FIG. 3 is a front elevational view of the eye shown in FIG. 2;

FIG. 4 is an elevational view of a bifocal IOL of the invention having a region of relatively enhanced optical power disposed asymmetrically on the IOL's anterior surface;

FIG. 5 is a schematic diagram of the IOL according to the invention (adapted for use in the right eye of a human), with Cartesian axes centered about the IOL;

DETAILED DESCRIPTION

Figure 6:
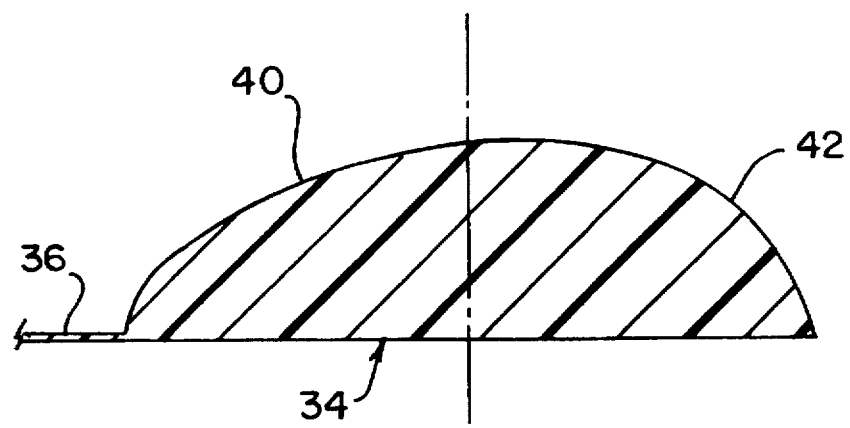
FIG. 6 is a cross-sectional side view of the IOL of FIG. 4 taken along line 6—6 of FIG. 4 and looking in the direction of the arrows in which the posterior surface is simply illustrated as planar.

With reference to FIG. 1, the normal human eye 10 includes a cornea 12, an iris 14, a pupil 16, a lens 18, a retina 20, and an optic nerve 22. In the normal eye, light is transmitted through the cornea 12, the pupil 16, and the lens 18, and is focussed by these elements onto the retina 20.

In the treatment of cataracts, for example, an incision 30 is made at the point where the cornea 12 and the sclera 32 meet, as illustrated in FIGS. 2 and 3, and the cataractous lens 18 is removed. A new IOL 34 is then inserted into the eye 10 to replace the light focusing functions which previously had been carried out by the lens 18. As illustrated most clearly in FIG. 2, the IOL 34 is inserted behind the iris 14. This type of lens is known as a posterior chamber lens. However, also known are anterior chamber lenses, which are placed in area 37 between the cornea 12 and the iris 16, and iris-plane lenses, which are inserted into the area of the pupil 16, both of which may be manufactured in accordance with the subject invention for placement in any of these positions in the eye.

As shown in FIG. 4, the IOL 34 of this embodiment of the invention usually has a generally circular contour with a diameter of approximately 5.5 to 6.0 mm (dimension a). Other shapes for the IOL 34 may be appropriate for focusing images onto the retina 20. Haptics 36 and 38 function as legs which support the IOL 34 in a desired position in the posterior chamber of the eye. Each haptic 36, 38 may extend approximately 4 mm or less from the IOL 34 (dimension b). Thus, the total pre-implantation length of the IOL 34 and haptics 36 and 38 may be approximately 14 mm, but the total length is adaptable for reliable placement of the lens within the desired location in the eye 10.

As used herein, an "aspheric" IOL means that the radius of curvature along at least one IOL 34 "meridian" (which is an imaginary line on the IOL surface passing through the geometric center of the IOL, analogous to a geographic meridian) is not a constant. Also as used herein, "asymmetric" means that the profile of the IOL curvature along at least one half-meridian is not the same as (i.e., it is not a mirror image of) the other half of the same meridian. The degree of asymmetry of the IOL 34 is directly attributable to the size of the second optical region 42, discussed below.

According to the invention, an optical surface of increased dioptric power is provided on the periphery of the inferior nasal portion of the IOL 34, that is, with respect to the eye in which the lens is implanted and does not extend over the entire IOL peripheral region. With reference now to FIG. 5, the IOL 34 (adapted for a right eye) is illustrated in schematic form, the contours of the anterior surface 50 being disregarded for clarity. The IOL has a body portion 52 and a peripheral portion 54. The peripheral portion 54 extends to an edge 56, which typically, but not necessarily demarks the boundary of the anterior surface 50 and a posterior surface 58 (not shown), to a union 60 (shown in phantom) with the body portion 52. Preferably, the peripheral and body portions 54, 52 define a seamless, transparent union 60. The relative power and extent (e.g., diameter) of the body portion 52 is chosen based on individual patient considerations, as well known in the art.

By way of illustration, Cartesian x and y axes are illustrated as crossing within the body portion 52 to define four quadrants, respectively labelled inferior nasal quadrant ("INQ"), superior nasal quadrant ("SNQ"), inferior temporal quadrant ("ITQ"), and superior temporal quadrant ("STQ"). These quadrants of the IOL 34 are labeled to correspond to the quadrants of the eye 10 into which the IOL 34 is implanted. According to the invention, only a limited portion of the lens has the enhanced optical power required for reading or other near-field activities (such as personal hygiene, cooking, etc.). Preferably, the surface of increased dioptric power is limited substantially to that portion of the inferior nasal quadrant that lies within the peripheral portion 54. However, all that is important to the invention is that a second optical region of increased dioptric power relative to a first optical region be asymmetrically disposed on one of the IOL 34's anterior or posterior surfaces 50, 58. Again, the relative size of the body and peripheral portions 52, 54 should be chosen with reference to individual patient considerations.

With reference now to FIG. 4, IOL 34 has first and second optical regions 40, 42 of first and second refractive powers, respectively. The second optical region 42 (having greater refractive power) occupies a relatively small portion of the anterior (the outwardly facing) surface of the lens whereas the first optical region 40 (having lesser refractive power) occupies the remainder of the anterior surface of the IOL 34. Preferably, the second optical region 42 is positioned substantially within the inferior nasal quadrant of the peripheral portion 54 of the IOL 34. The second optical region 42 may, but does not need to, extend to the edge 56. Thus, according to this preferred embodiment, FIG. 4 illustrates an IOL 34 adapted to be inserted into the right eye of the patient. An IOL 34 adapted to be inserted into the patient's left eye would essentially be a mirror image of FIG. 4. Either or both of the first and second optical regions 40 and 42 may be formed with equal advantage and facility on the posterior surface of the IOL 34.

While it is generally preferred that the second optical region 42 span the INQ substantially within the peripheral portion 54 of the IOL 34, the invention is not so limited. The second optical region 42 may span an arc length of somewhat more than 90°, for example, 30°–100°. As illustrated, the surface of the second optical region 42 has a generally convex shape.

The first and second optical regions 40 and 42, being of differing refractive power, provide a bifocal intraocular IOL 34. The refractive power of the second optical region 42 may exceed that of the remainder of the IOL 34 by any number of diopters, e.g., three or more diopters as requested. For example, the body portion 52 of the IOL 34 and the peripheral portion 54 that is clear of the optical region 42 together have a refractive power defined by the first optical region 40. It is through this body portion 52 that most of the light rays pass. The body portion 52 may have a strength of eighteen diopters in water whereas the asymmetric second optical region 42 (within the INQ of the peripheral portion 54) may provide twenty-two diopters in water. (The aqueous medium in the eye that surrounds the lens and, after surgery, the IOL 34 has essentially the optical properties of water.)

The body portion 52 of the IOL 34 is preferably spherical. The second optical region 42 is preferably disposed substantially within the peripheral portion 54 of the IOL 34, between nine o'clock and six o'clock for the patient's left IOL and between six o'clock and three o'clock for the patient's right IOL. The part of the peripheral portion 54 outside region 42 has a focal length defined by the first optical region 40. This positioning ensures that the enhanced refractive power of second optical region 42 is disposed within and is preferably substantially coextensive with the INQ. The second optical region 42 provides a focal length to the bifocal IOL 34 that differs from that of the first optical region 40, and is asymmetrically disposed on the IOL 34 because no corresponding region is provided on an opposite side of the IOL 34, for example, on the superior temporal side of the IOL 34. As a result, the undesirable blur, loss of contrast sensitivity, halo, and the combination of these effects that have been associated with known bifocal IOLs for far-field viewing are substantially eliminated because, while viewing far-field objects, relatively few light rays pass through the second optical region 42 of the IOL 34, while substantially all of the light rays required for near-field activities pass through this portion.

Whether the peripheral portion 54 of the region 40 of the IOL 34 is spherical or aspherical depends on individual patient considerations. The topology of the remainder of IOL 34 is unrelated to the power of the second optical region 42. Also, whether to provide a toric surface for the remainder of the IOL and at what orientation is partially dependent on corneal topography, as well as on the astigmatism produced by the surgeon performing the operation.

FIG. 6 illustrates, in cross-section, a further feature of the second optical region 42. The second optical region 42 preferably has progressively increasing optical power in the outwardly radial direction toward the edge of the IOL 34. The progressively increasing power is achieved, in this embodiment, by providing a progressively steeper arc radius in a radial direction toward the edge 56 in the form of a blended aspheric curve. The blended aspheric curve comprises multiple arc radii forming a surface that is free of bumps or discontinuities in the radial direction which, if present, would prevent a smooth transition of the optical power and provide a surface upon which debris may accumulate. In contrast, the optical power region 40, which may span approximately 270° of the IOL 34, has a uniform arc radius. The light incident on the second optical region 42 is such that the central nervous system can select from among the incident light rays the near-field image that is most in focus. This is an autonomic function of the central nervous system, facilitated by the power gradient of the second optical region 42. While the IOL 34 shown in FIG. 6 is formed from a plano-convex blank, the IOL 34 can be formed as a double-convex structure, as shown in FIG. 7 and described below, or from plano-concave blanks, etc.

Alternatively, the second optical region 42 may comprise a diffractive element that provides relatively increased dioptric strength as compared to the optical region 40.

A toric surface may also be provided, to correct for and negate any astigmatism, including any astigmatism introduced by the surgery itself, as understood by those skilled in the art. Preferably the toric surface is disposed on a surface of the IOL 34 opposite the first and second optic regions 40 and 42 (e.g., if regions 40 and 42 are on the anterior surface, the toric surface is preferably constructed on the posterior lens surface). The toric surface may extend into the body portion 52. For methods of offsetting surgery-induced astigmatism, see U.S. Pat. No. 4,512,039 to Lieberman, the disclosure of which is hereby incorporated by reference as though set forth herein.

Figure 7A:
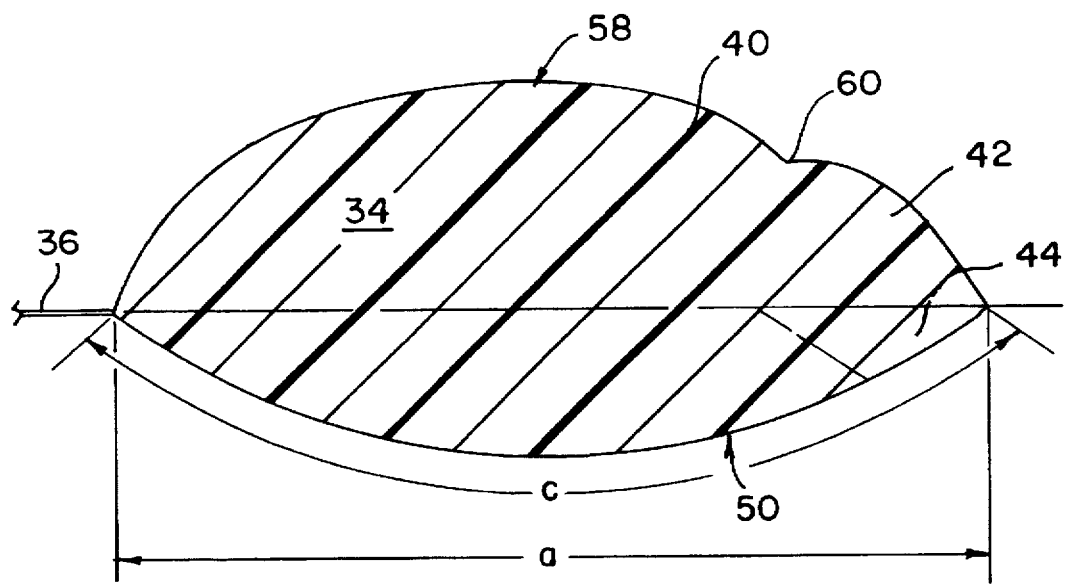
FIG. 7A is an orthogonal cross-sectional side view taken along line 7A—7A of FIG. 4 and looking in the direction of the arrows, additionally (optionally) modified to have a toric posterior surface.
Figure 7B:
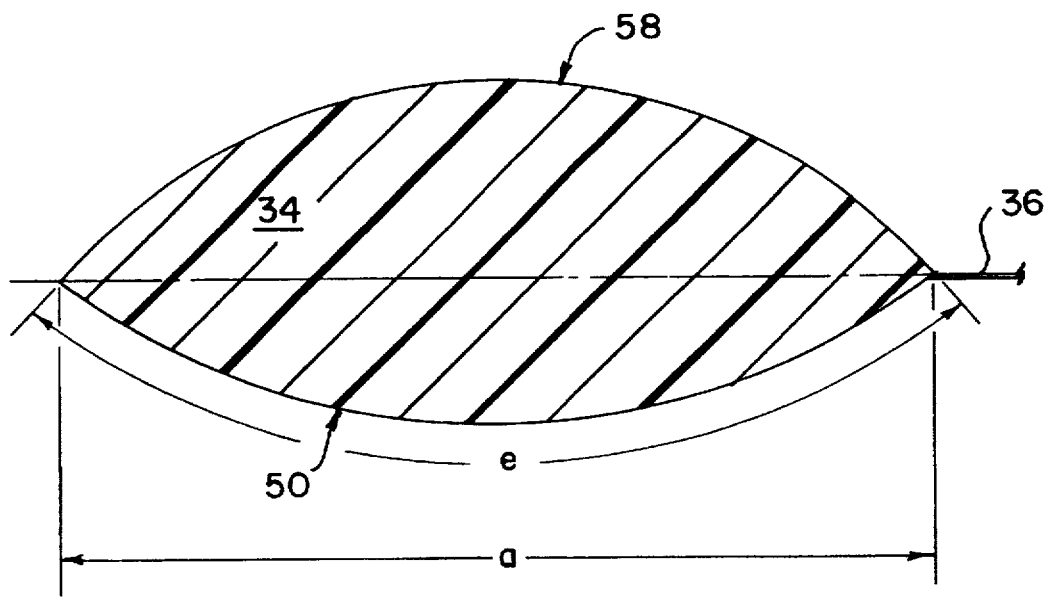
FIG. 7B is an orthogonal cross-sectional side view taken along line 7B—7B of FIG. 4 and looking in the direction of the arrows, additionally (optionally) modified to have a toric posterior surface.

The toric surface may be formed on a surface of the IOL 34, and preferably on the posterior surface, as shown in FIGS. 7A and 7B. Conceptually, the IOL 34 has major arc lines or meridians spanning from one peripheral edge to an opposite edge along each of the posterior and anterior surfaces 58, 50. A vertical meridian is a meridian corresponding to the 6:00 position of the lens (or the eye cornea);

a horizontal meridian is at right angles to the vertical meridian. The IOL 34 may be formed such that one of the vertical meridian (arc "c" in FIG. 7A) or the horizontal meridian (arc "e" in FIG. 7B) is optically weaker than the other. The contours of the arcs "c" and "e" influence the light refracting characteristics of the IOL 34. Accordingly, the surgeon selects a IOL 34 having the desired calculated difference in strength between these two, generally orthogonal, meridians. To offset astigmatism that may have existed prior to surgery, as well as astigmatism induced by surgery, the selected IOL 34 is oriented in the eye so that the refractive power differences along the vertical and along the horizontal meridians are effective to offset the astigmatism. While the toric surface may be disposed on the same surface of the IOL 34 as the bifocal optics, the resulting geometry will be more complex. Accordingly, it is preferred to provide the toric surface on the IOL surface that does not contain surface 42. The ability to provide a toric surface on the IOL 34 allows the astigmatism of patients with post-surgery astigmatism or both pre- and post-surgery astigmatism to be treated, and serves to increase visual acuity without the assistance of spectacles.

Figure 8:
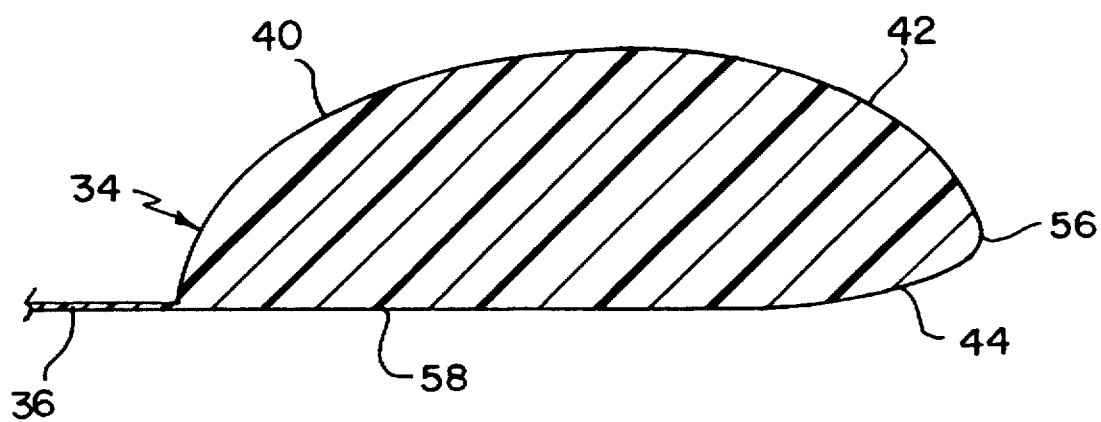
FIG. 8 is a cross-sectional side view taken along line 8—8 of FIG. 4 and looking in the direction of the arrows, modified to have a prism on its posterior surface.

According to another aspect of the invention, a prism 44 provides a "base-out" curvature to counteract the inherent "base-in" curvature of the convex IOL 34. Convex lenses such as the IOL 34 have an inherent "base-in" prismatic effect, as previously described. Ideally, however, light should be reflected toward the person's nose to aid in reflex convergence. The prism 44 illustrated in FIG. 8 has a base formed as a blended curve that spans an arc segment of the peripheral portion 54 along the edge 56. The apex of the prism 44 preferably coincides with the radially inwardmost portion of the second optical region 42, in the vicinity of the union 60, on the opposite side of the IOL 34. The base-out curvature of the prism 44 provides a desirable assist to the convergence reflex when viewing near-field objects. Thus, the prism 44 is provided to bend incident light towards the patient's nose. As shown in FIG. 8, the prism 44 is preferably disposed on a surface of the IOL 34 opposite the second optical region 42. When the surface having the prism 44 is toric, it is preferred that the prism 44 be formed together with the toric surface. That portion of the surface having the prism 44 that does not embody the prism 44 itself, is either spherical or toric in shape. In FIG. 8, the IOL 34 is illustrated as biconvex and has the prism 44 disposed on the posterior surface 58, as shown in phantom.

Each of the features of the bifocal IOL 34 can be achieved by ablating, or milling, or otherwise showing a lens blank. One preferred way for making the bifocal IOL 34 is the use of the so-called "ASTIGMATIC" from EuroPrecision Technology, [Venray], Netherlands. Such a lathe or other device preferably uses a modulated sine wave to create the mechanical lathe stroke that will govern the shape of the IOL 34 that is to be formed from the lens blank, according to the manufacturer's instructions.

Preferably, the IOL 34 having the second optical region 42 is constructed so that it also includes either the toric surface, the prism 44, or both. Advantageously, the IOL 34 is constructed in accordance with a two-of-three rule in which no more than two of these features resides on a given surface of the IOL 34. Thus, for example, the toric and prism 44 features may reside on the posterior surface while the high power region 42 resides on the anterior surface, substantially opposite the prism 44. Preferably, the prism is integrally formed with the toric surface when a toric surface is included in the IOL 34.

Having thus described a preferred embodiment of the present invention, it is to be understood that the above described device and method is merely illustrative of the principles of the present invention, and that other devices may be devised by those skilled in the art without departing from the spirit and scope of the invention as claimed below.

I claim:

1. An intraocular lens for implantation into an eye, comprising:
   an optical surface including a central portion and a peripheral portion;
   a first refractive power region within at least said central portion; and
   a second refractive power region substantially concentrated only in one predetermined location within said peripheral portion on a nasal side of the intraocular lens relative to the eye upon implantation into the eye, said second refractive power region being of greater refractive power than said first refractive power region.

2. An intraocular lens as in claim 1, wherein said first refractive power region is constructed for focusing far-field images on the retina of the eye, and said second refractive power region is constructed for focusing near-field images on the retina of the eye.

3. An intraocular lens as in claim 1, wherein said first refractive power region occupies a region of said peripheral portion outside said second refractive power region.

4. An intraocular lens as in claim 1, wherein said optical surface is one of an anterior and a posterior surface, said anterior and posterior surfaces being separated by an edge, and wherein said second refractive power region extends radially inwardly from one said edge of the intraocular lens.

5. An intraocular lens as in claim 1, wherein said second refractive power region is adapted to occupy at least a part of the peripheral portion within the inferior nasal quadrant of the intraocular lens relative to the eye.

6. An intraocular lens as in claim 1, wherein said optical surface is an anterior surface, and wherein said second refractive power region is disposed on said anterior surface of the intraocular lens.

7. A bifocal intraocular lens as in claim 1, wherein said optical surface is a posterior surface, and wherein said second refractive power region is disposed on said posterior surface of the intraocular lens.

8. An intraocular lens as in claim 1, the multifocal intraocular lens having anterior and posterior surfaces, and further comprising a toric surface having vertical and horizontal meridians of differing optical strength disposed on one of said anterior and posterior surfaces.

9. An intraocular lens as in claim 8, wherein said toric surface is on the one of the anterior and posterior surfaces of the intraocular lens that does not include at least one of said first and second refractive power regions.

10. An intraocular lens as in claim 1, the intraocular lens having anterior and posterior surfaces, further comprising a prism disposed on one of said anterior and posterior surfaces.

11. An intraocular lens as in claim 10, wherein said prism is disposed on a posterior surface of the intraocular lens.

12. An intraocular lens as in claim 10, wherein said prism is disposed on an anterior surface of the intraocular lens.

13. An intraocular lens as in claim 10, wherein said prism is disposed on the one of the anterior and posterior surfaces of the intraocular lens that does not include said second refractive power region.

14. An intraocular lens as in claim 1, wherein said second refractive power region occupies substantially only a nasal side of the intraocular lens relative to the eye upon implantation into the eye.

15. An intraocular lens both for focusing images on a retina of an eye and for correcting astigmatism, the intraocular lens including a peripheral portion and a nasal quadrant, comprising:

anterior and posterior surfaces;

first and second refractive power regions on one of said anterior and posterior surfaces, said first refractive power region being constructed for focusing far-field images on the retina, and said second refractive power region being constructed for focusing near-field images on the retina, said second refractive power region being asymmetrically disposed on the peripheral portion of the inferior nasal quadrant of the intraocular lens; and another of said anterior and posterior surfaces being torically shaped and having first and second meridians, one of said first and second meridians being optically weaker than the other.

16. An intraocular lens as in claim 15, wherein the intraocular lens has a central portion outside said second refractive power region.

17. An intraocular lens as in claim 15, wherein said second refractive power region spans the peripheral portion of the inferior nasal quadrant of the intraocular lens.

18. An intraocular lens as in claim 15, further comprising a prism disposed on the other of said anterior and posterior surfaces and opposite said second refractive power region.

19. An intraocular lens as in claim 18, wherein said prism is disposed on the posterior surface of the intraocular lens and said second refractive power region is disposed on the anterior surface.

20. An intraocular lens for implantation into an eye, comprising:

an optical surface including a central portion and a concentric peripheral portion;

first and second refractive power regions disposed on said optical surface, said second refractive power region being of greater refractive power than said first refractive power region;

said second refractive power region being asymmetrically located with respect to said central portion substantially within said peripheral portion and being substantially concentrated only within one quadrant at a predetermined location on a nasal side of the intraocular lens relative to the eye upon implantation into the eye.

21. An intraocular lens as in claim 20, wherein said second refractive power region is disposed in an inferior nasal quadrant of the intraocular lens relative to the eye.

* * * * *